United States Patent [19]

Hastings et al.

[11] Patent Number: 5,780,263

[45] Date of Patent: Jul. 14, 1998

[54] HUMAN CCN-LIKE GROWTH FACTOR

[75] Inventors: Gregg A. Hastings, Germantown; Mark D. Adams, North Potomac, both of Md.

[73] Assignee: Human Genome Sciences, Inc., Rockville, Md.

[21] Appl. No.: 468,847

[22] Filed: Jun. 6, 1995

[51] Int. Cl.$^6$ .................................................. C12N 15/12
[52] U.S. Cl. .................. 435/69.1; 435/252.3; 435/320.1; 435/325; 536/23.5
[58] Field of Search ...................... 536/23.5; 435/320.1, 435/240.2, 252.3, 69.1

[56] References Cited

PUBLICATIONS

FEBS 12753, vol. 327, No. 2, Bork, issued Jul. 1993, pp. 125–130.
Genomics, vol. 16, Chen, et al., issued 1993, pp. 533–535.
Journal of Cell Biology, vol. 114, No. 6, issued Sep. 1991, Bradham, et al., pp. 1285–1294.
Proc. Natl'l. Acad. Sci. USA, vol. 86, issued Feb. 1989, Simmons, et al., pp. 1178–1182.
EMBL–Genbank, pub. May 18, 1995, Hillier, et al., Locus R52804.
EMBL–Genbank, pub. Jan. 4, 1995, Adams, et al., Locus T31748.
EMBL–Genbank, pub. Jan. 4, 1995, Adams, et al., Locus T31716.
EMBL–Genbank, pub. Nov. 6, 1994, Genexpress, Locus HSC29F031.
EMBL–Genbank, pub. Jun. 4, 1993, Genexpress, Locus HSA06A062.

*Primary Examiner*—Stephen Walsh
*Assistant Examiner*—Karen E. Brown
*Attorney, Agent, or Firm*—Elliot M. Olstein; J. G. Mullins

[57] ABSTRACT

A human Small CCN-Like Growth Factor polypeptide (SCGF) and DNA (RNA) encoding such polypeptide and a procedure for producing such polypeptide by recombinant techniques is disclosed. Also disclosed are methods for utilizing such polypeptide for wound healing or tissue regeneration, stimulating implant fixation and angiogenesis. Antagonist against such polypeptides and their use as a therapeutic to treat atherosclerosis, tumors and scarring are also disclosed. Diagnostic assays for identifying mutations in SCGF nucleic acid sequences and altered levels of the SCGF polypeptide are also disclosed.

20 Claims, 6 Drawing Sheets

FIG. 1A

```
1   CGCCAAACCTCTATGGATATATAAAGGAAGCTTGAGGAGGAATTTCACAGTTACAGTGC       60
61  AGAAGCAGAGGCAAAAGAATTAACCAGCTCTTCAGTCAAGCAAATCCTCTACTCACCATG    120
                                                               M      1

121 CTTCCTCCTGCCATTCATTTCTATCTCCCTTGCATGCATCCTAATGAAAAGCTGT         180
    L  P  P  A  I  H  F  Y  L  L  P  L  A  C  I  L  M  K  S  C       21

181 TTGGCTTTTAAAAATGATGCCACAGAAATCCTTTATTCACATGTGGTTAAACCTGTTCCA    240
    L  A  F  K  N  D  A  T  E  I  L  Y  S  H  V  V  K  P  V  P      41

241 GCACACCCCAGCAGCAACAGCACGTTGAATCAAGCCAGAAATGGAGGCAGGCATTTCAGT    300
    A  H  P  S  S  N  S  T  L  N  Q  A  R  N  G  G  R  H  F  S      61

301 AACACTGGACTGGATCGGAACACTCGGGTTCAAGTGGTTGCCGGGAACTGCGTTCCACC    360
    N  T  G  L  D  R  N  T  R  V  Q  V  G  C  R  E  L  R  S  T      81

361 AAATACATCTCTGATGGCCAGTGCACCAGCATCAGCCCTCTGAAGGAGCTGGTGTGTGCT    420
    K  Y  I  S  D  G  Q  C  T  S  I  S  P  L  K  E  L  V  C  A     101
```

FIG. 1B

```
421 GGCGAGTGCTTGCCCCTGCCAGTGCTCCCTAACTGGATTGGAGGAGGCTATGGAACAAAG  480
102  G  E  C  L  P  L  P  V  L  P  N  W  I  G  G  G  Y  G  T  K   121

481 TACTGGAGCAGGAGGAGCTCCAGGAGTGGCGGTGTGTCAATGACAAAACCCGTACCCAG   540
122  Y  W  S  R  R  S  S  Q  E  W  R  C  V  N  D  K  T  R  T  Q   141

541 AGAATCCAGCTGCAAGATGGCACAGCCACCTACAAAATCACAGTAGTCACT          600
142  R  I  Q  L  Q  C  Q  D  G  S  T  R  T  Y  K  I  T  V  V  T   161

601 GCCTGCAAGTGCAAGAGTACACCCGGCAGCAGTCCAGTCACAACTTTGAGAGC         660
162  A  C  K  C  K  R  Y  T  R  Q  H  N  E  S  S  H  N  F  E  S   181

661 ATGTCACCTGCCAAGCCTGTCCAGCATCACAGAGAGCGAAAAGAGCCAGCAAATCCAGC   720
182  M  S  P  A  K  P  V  Q  H  H  R  E  R  K  R  A  S  K  S  S   201

721 AAGCACAGCATGAGTTAGAACTCAGACTCCCATAACTAGACTTACTAGTAACCATCTGCT  780
202  K  H  S  M  S  *                                              206

781 TTACAGATTTGATTGCTTGGAAGACTCAAGCCTGCCACTGCTGTTTCTCACTTGAAAGT   840
841 ATATGCTTTCTGCTTTGATCAAACCCAGCAAGCTGTCTTAAGTATCAGGACCTTCTTTGG  900
```

FIG. 2A

```
cyr6_mouse   ..........M  SSSTFRTLAV  AVTLLHLTRL  AL.STCP...  ..AACHCP..
       HCGF  ..........M  SSRIVRELAL  VVTLLHLTRV  GL.STCP...  ..ADCHCP..
 ce10_chick  ........M    GSAGARP.AL  AAALLCLARL  ALGSPCP...  ..AVCQCP..
 ctgf_human  ........MTA. ASMGPVRVAF  VVLLALCSRP  AVGQNCS...  ..GPCRCPD.
    fisp-12  ........MLA  SVAGPISLAL  .VLLALCTRP  ATGQDCS...  ..AQCQCAA.
  nov_chick  METGGG....   ..QGLPVLL   LLLLLLRPCE  VSGREAA...  ..CPRPCGGR
       HNGF  MQSVQSTSFC   LRKQCLCLTF  LLLHLLGQVA  ATQR......  ..CPPQCPGR
       VIGF  ..........   ....MKSVL.  LLTTLLVPAH  LVAAWSNNYA  VDCPQHCDSS
 ibp3_human  ........MQR  ARPTLWAAAL  TLLVLLRGPP  VARAGASSGG  LGPVVRCEPC
       SCGF  ..........   ..........  ..........  ..........  ..........

111
cyr6_mouse   GLECNFGASS   TALKGICRAQ  SEGRPCEYNS  RIYQNGESFQ  PNCKHQCTCI
       HCGF  GLECNFGASS   TALKGICRAQ  SEGRPCEYNS  RIYQNGESFQ  PNCKHQCTCI
 ce10_chick  GLECNFGASP   AATNGICRAQ  SEGRPCEYNS  KIYQNGESFQ  PNCKHQCTCI
 ctgf_human  GLFCDFGSPA   NRKIGVCTAK  .DGAPCIFGG  TVYRSGESFQ  SSCKYQCTCL
    fisp-12  GLFCDFGSPA   NRKIGVCTAK  .DGAPCVFGG  SVYRSGESFQ  SSCKYQCTCL
  nov_chick  GLYCDRGPED   GGGAGICMVL  .EGDNCVFDG  MIYRNGETFQ  PSCKYQCTCR
       HNGF  GLYCDRSADP   SNQTGICTAV  .EGDNCVFDG  VIYRSGEKFQ  PSCKFQCTCR
       VIGF  GE....DPFG   EEFGICKDCP  YGT.....FG  MDCRETCNCQ  SGICDRGTGK
 ibp3_human  DEARPLQALL   DGRGLCVNAS  AVSRLRAYLL  PAPPAPGNAS  ESEEDRSAGS
       SCGF  ..........   ..........  ..........  ..........  ..........
```

FIG. 2B

```
..LEAPKCAP GVGLVR......  .DGCGCCKVC AKQLNED...  ..........  .........C SKTQPCDHTK
..LEAPKCAP GVGLVR......  .DGCGCCKVC AKQLNED...  ..........  .........C RKTQPCDHTK
..AAAPQCAP GVGLVP......  .DGCGCCKVC AKQLNED...  ..........  .........C SRTQPCDHTK
..EPAPRCPA GVSLVL......  .DGCGCCRVC AKQLGEL...  ..........  .........C TERDPCDPHK
..EAAPHCPA GVSLVL......  .DGCGCCRVC AKQLGEL...  ..........  .........C TERDPCDPHK
CPAEPPRCAP GVPAVL......  .DGCGCCLVC ARQRGES...  ..........  .........C SPLLPCDESG
CPATPPTCAP GVRAVL......  .DGCSCCLVC ARQRGES...  ..........  .........C SDLEPCDESS
ECKSSPRCKR TVL.........  .DDCGCCRVC AAGRGETCYR  TVSGMDGMKC  GPGLRCQPSN
DARALAQCAP PPAVCAELVR    EPGCGCCLTC ALSEGQPC..  ...GIYTERC  GSGLRCQPSP
CL........ ...........  .......... ..........  ..........  ..........

220
D.GAVGCIPL CPQELSLPNL    GCPNPRLVKV SGQCCEEWVC  DEDSIKDSLD  DQDDL....L
GWRRGACIPL CPQELSLPNL    GCPNPRLVKV TGQCCEEWVC  DEDSIKDPME  DQDGLLGKGL
D.GAVGCIPL CPQELSLPNL    GCPSPRLVKV PGQCCEEWVC  DES..KDALE  ELEGFFSKEF
D.GAVGCMPL CSMDVRLPSP    DCPFPRRVKL PGKCCEEWVC  DEP.......  ..KDQTVVGP
D.GAVGCVPL CSMDVRLPSP    DCPFPRRVKL PGKCCKEWVC  DEP.......  ..KDRTAVGP
D.GQIGCLPR CNLGLLLPGP    DCPFPRKIEV PGECCEKWVC  DPR.......  ..DEVLLGGF
D.GQIGCVPR CQLDVLLPEP    NCPAPRKVEV PGECCEKWIC  GPD.......  ..EEDSLGGL
CL........ ...........  ..KFPFFQYS VTKSSNRFVS  LTEHDMASGD  GNIVREEVVK
VESPSVSSTH RVSDPKFHPL    HSKIIIKKG HAKDSQRYK.  .VDYESQSTD  TQNFSSESKR
.......... ...........  .......... ..........  ..........  ..........
```

FIG. 2C

```
cyr6_mouse   GLDASEVELT RNNELIAIGK GSSLKRLPVF GTEP..RVLF NPLHAHGQKC
      HCGF   GFDASEVELT RNNELIAVGK GSSLKRLPVF GMEP..RILY NPL..QGQKC
 ce10_chick  GLDASEGELT RNNELIAIVK G.GLKMLPVF GSEPQSRAFE NP.......KC
 ctgf_human  ALAAYRLEDT .......... .......... .F GPDPTMI... .......RANC
     fisp-12 ALAAYRLEDT .......... .......... .F GPDPTMM... .......RANC
  nov_chick  AMAAYRQEAT .......... .......... .L GIDVSDS... .......SANC
       HNGF  TLAAYRPEAT .......... .......... .L GVEVSDS... .......SVNC
       VIGF  ENAAGSPVMR KWLNPR.... .......... .......... ..........
 ibp3_human  ETEYGPCRRE MEDTLNHLKF LNVLSPRGVH IPNCDKKGFY KKKQCRPSKG
       SCGF  ...MLPPAIH FYLLPLACIL MKSCLAFKND ATEILYSHVV KPVPAHPSSN 331
cyr6_mouse   TKKSPEPVRF TYAGCSSVKK YRPKYCGSCV DGRCCTPLQT RTVKMRFRCE
      HCGF   TKKSPEPVRF TYAGCLSVKK YRPKYCGSCV DGRCCTPQLT RTVKMRFPCE
 ce10_chick  TKKSPSPVRF TYAGCSSVKK YRPKYCGSCV DGRCCTPQQT RTVKIRFRCD
 ctgf_human  TPKISKPIKF ELSGCTSMKT YRAKFCGVCT DGRCCTPHRT TTLPVEFKCP
     fisp-12 TPKIAKPVKF ELSGCTSVKT YRAKFCGVCT DGRCCTPHRT TTLPVEFKCP
  nov_chick  TKKSMKAVRF EYKNCTSVQT YKPRYCGLCN DGRCCTPHNT KTIQVEFRCP
       HNGF  TKKSLKAIHL QFKNCTSLHT YKPRFCGVCS DGRCCTPHNT KTIQAEFQCS
       VIGF  .......... .......... .......... .......... ..........
 ibp3_human  .......... .......... .......... .......... ..........
       SCGF  ....PLPVLP NWIGGYGTK  YWSR...RSS QEWRCVNDKT RTQRIQLQCQ
```

FIG. 2D

```
IVQTTSWSQC SKSCGTGIST RVTNDNPECR LVKETRICEV RPCGQPVY.S SLKKGKKCSK
IVQTTSWSQC SKTCGTGIST RVTNDNPECR LVKETRICEV RPCGQPVY.S SLKKGKKCSK
IVQTTSWSQC SKTCGTGIST RVTNDNPDCK LIKETRICEV RPCGQPSY.A SLKKGKKCTK
LVQTTEWSAC SKTCGMGIST RVTNDNASCR LEKQSRLCMV RPCEADLEE. NIKKGKKCIR
LVQTTEWSAC SKTCGMGIST RVTNDNTFCR LEKQSRLCMV RPCEADLEE. NIKKGKKCIR
IEQTTEWSAC SKSCGMGFST RVTNRNQQCE MVKQTRLCMM RPCEN..EEP SDKKGKKCIQ
IEQTTEWTAC SKSCGMGFST RVTNRNRQCE MLKQTRLCMV RPCEQEPEQP TDKKGKKCLR
.......... .......... .......... .......... .......... ..........
RKRGFCWCVD KYGQPLPGYT TKGKEDVHCY SMQSK..... .......... ..........
STLNQARNGG RHFSNTGL.D RNTRVQVGCR ELRSTKYISD GQCTSISPLK ELVCAGECL.

438
DGEMFSKNVM MIQSCKCNYN CPHPNEASFR LYSLFNDIHK FRD....... ..........
DGETFSKNVM MIQSSKCNYN CPHANEAAFP FYRLF..... .......... ..........
DGETFTKSVM MIQSCRCNYN CPHANEA.YP FYRLVNDIHK FRD....... ..........
DGEVMKKNMM FIKTCACHYN CPGDND.IFE SLYYRKMYGD MA........ ..........
DGEIMKKNMM FIKTCACHYN CPGDND.IFE SLYYRKMYGD MA........ ..........
QGKFLKKPMM LINTCVCHGN CPQSNNAFFQ PLDPMSSEAK I......... ..........
PGQIVKKPVM VIGTCTCHTN CPKNNEAFLQ ELELKTTRGK M......... ..........
.......... .......... .......... .......... .......... ..........
DGSTRTYKIT VVTACKCKRY TRQHNESSHN FESMSPAKPV QHHRERKRAS KSSKHSMS
```

HUMAN CCN-LIKE GROWTH FACTOR

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as a human small CCN-like Growth Factor, sometimes hereinafter referred to as "SCGF". The invention also relates to inhibiting the action of such polypeptides.

The polypeptide of the present invention is related to a family of growth regulators comprising cef 10/cyr 61, connective tissue growth factor (CTGF), and nov. The mRNA corresponding to the polypeptide of this invention is highly expressed in the kidney, lung, heart and brain, with the abundance in that order.

Growth factors and other mitogens, including transforming oncogenes, are capable of rapidly inducing a complex set of genes to be expressed by certain cells (Lau, L.F. and Nathans, D., *Molecular Aspects of Cellular Regulation*, 6:165–202 (1991). These genes, which have been named immediate early or early response genes, are transcriptionally activated within minutes after contact with a growth factor or mitogen, independent of de novo protein synthesis. A group of these immediate early genes encodes secreted, extracellular proteins which are needed for coordination of complex biological processes such as differentiation and proliferation, regeneration and wound healing (Ryseck, R.P. et al, *Cell Growth Differ.*, 2:235–233 (1991).

Highly related proteins which belong to this group include cef 10 from chicken, which was detected after induction by the viral oncogene pp60$^{v-arc}$ (Simmons, D.L. et al., *PNAS*, U.S.A., 86:1178–1182 (1989). A closely related protein, cyr 61, is rapidly activated by serum or platelet-derived growth factor (PDGF) (O'Brien, T.P. et al., *Mol. Cell Biol.*, 10:3569–3577 (1990). The overall amino acid identity between cef 10 and cyr 61 is as high as 83%. A third member is human connective tissue growth factor (CTGF) (Bradham, D.M. et al., *J. Cell. Biol.*, 114:1285–1294 (1991). CTGF is a cysteine-rich peptide which is secreted by human vascular endothelial cells in high levels after activation with transforming growth factor beta (TGF-β). CTGF exhibits PDGF-like biological and immunological activities and competes with PDGF for a particular cell surface receptor.

A fourth member of the immediate-early proteins is fisp-12, which has been shown to be induced by serum and has been mapped to a region of the reurine genome (Ryseck, R.P. et al., *Cell Growth Differ.*, 2:235–233 (1991). Yet another member of this family is the chicken gene, nov, normally arrested in adult kidney cells, which was found to be overexpressed in myeloblastosis-associated virus type 1 induced nephroblastomas. Further, expression of an amino-terminal-truncated nov product in chicken embryo fibroblasts was sufficient to induce transformation (Joliot, V. et al., *Mol. Cell. Biol.*, 12:10–21 (1992).

The expression of these immediate early genes act as "third messengers" in the cascade of events triggered by growth factors. It is also thought that they are needed to integrate and coordinate complex biological processes, such as differentiation and wound healing in which cell proliferation is a common event.

This emerging family of growth regulators is called the CCN family for CTGF; cef 10/cyr 61; and nov. The polypeptide of the present invention is thought to be a member of this family of growth regulators.

In accordance with one aspect of the present invention, there is provided a novel mature polypeptide, as well as biologically active and diagnostically or therapeutically useful fragments, analogs and derivatives thereof.

In accordance with another aspect of the present invention, there are provided isolated nucleic acid molecules encoding the polypeptide of the present invention including mRNAs, DNAS, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process of utilizing such polypeptide, or polynucleotide encoding such polypeptide for therapeutic purposes, for example, to treat muscle wasting diseases, osteoporosis, to aid in implant fixation, to stimulate wound healing and tissue regeneration, to promote angiogenesis and to stimulate proliferation vascular smooth muscle and endothelial cell production.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to limit the production of excess connective tissue during wound healing or pulmonary fibrosis.

In accordance with yet a further aspect of the present invention, there are also provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to the under-expression and over-expression of the polypeptide of the present invention and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA (SEQ ID NO:1) and corresponding deduced amino acid sequence (SEQ ID NO:2) of the polypeptide of the present invention. The initial 23 amino acids represent the putative leader sequence (underlined). The standard one letter abbreviations for amino acids are used. Sequencing was performed using a 373 Automated DNA sequencer (Applied Biosystems, Inc.).

FIG. 2 shows the amino acid sequence homology between the polypeptide of the present invention and other proteins which are members of the CCN family.

For comparison purposes portions of, or all of, the amino acid sequences for nine CCN protein family members are shown in FIG. 2 (SEQ ID NOS:11–20, respectively). The amino acid sequences in FIG. 2 are shown in comparison alignment as one-letter codes with spacing. However, for convenience of their listing, the one-letter codes have been changed to the three-letter codes and the spacing has been removed to list the respective amino acid sequences as continuous sequences in SEQ ID NOS:11–20.

In accordance with an aspect of the present invention, there are provided isolated nucleic acids (polynucleotides) which encode for the mature polypeptide having the deduced amino acid sequence of FIG. 1 (SEQ ID NO:2) or for the mature polypeptide encoded by the cDNA of the clone (s) deposited as ATCC Deposit No. 97173 on Jun. 2, 1995.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

A polynucleotide encoding a polypeptide of the present invention was discovered in a cDNA library derived from human 9 week embryo. It is structurally related to the CCN family. It contains an open reading frame encoding a protein of 206 amino acid residues of which the first 23 amino acids residues are the putative leader sequence such that the mature protein comprises 183 amino acids.

The designation of SCGF as a member of the CCN growth factor family was based primarily through conservation of amino acid sequences. The homology to the CCN family is approximately 27% with all the members. The highest similarity to CCN members is 62% over a 29 amino acid stretch of SCGF. The polypeptide of the present invention is cysteine-rich with 10 cysteines. It is about 50% the size of CTGF, cyr61 and nov.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID No. 2) or for the mature polypeptide encoded by the deposited CDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein, once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian hosto e.g., COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIG. 1 (SEQ ID NO:1) or the deposited cDNA(s), i.e. function as an SCGF polypeptide.

Alternatively, the polynucleotides may have at least 20 bases, preferably 30 bases and more preferably at least 50 bases which hybridize to a polynucleotide of the present invention and which have an identity thereto, as hereinabove described, and which does not retain activity. Such polynucleotides may be employed as probes for the polynucleotide of SEQ ID NO:1, or for variant thereof, for example, for recovery of the polynucleotide or as a diagnostic probe or as a PCR primer.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID No:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence or (v) splice variants of the mature polypeptide which are lacking certain amino acid residues yet still retain biological activity. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the SCGF genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*, lac or trp, the phage lambda PL promoter and other promoters known to control expression of genes in prokaryotic or eukaryotic cells or their viruses. The expression vector also contains a ribosome-binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, PBSKS, pNH8A, pNH16a, pNH18A, pNH46A (Stratagene); pTRC99a, pKK2233, pKK233-3, pDR540, pRIT5 (Pharmacia). Eukaryotic: PWLNEO, pSV2CAT, pOG44, PXT1, pSG (Stratagene) pSVK3, PBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda PRI PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAEDextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomanas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. polypeptides of the invention may also include an initial methionine amino acid residue.

The polypeptide of the present invention may be employed in wound-healing and associated therapies concerned with regrowth of tissue, such as connective tissue, skin, bone, cartilage, muscle, lung or kidney.

The polypeptide of the present invention may be employed for tissue remodeling such as restenosis, cardiac dilation/hypertrophy (congestive heart failure) and atherosclerosis.

The polypeptide may also be employed to stimulate angiogenesis, for example, to enhance the growth of vascular smooth muscle and endothelial cells. The increase in angiogenesis would be beneficial to ischemic tissues and to collateral coronary development in the heart subsequent to coronary stenosis.

The polypeptide of the present invention may also be employed during implant fixation to stimulate the growth of cells around the implant and therefore, facilitate its attachment to its intended site.

The polypeptide of the present invention may be employed to stimulate early growth of an embryo, since the expression pattern of the SCGF polypeptide is abundant in embryonic libraries.

In accordance with yet a further aspect of the present invention, there is provided a process for utilizing such polypeptides, or polynucleotides encoding such polypeptides, as a research reagent for in vitro purposes related to scientific research, synthesis of DNA and manufacture of DNA vectors, for the purpose of developing therapeutics and diagnostics for the treatment of human disease.

This invention provides a method for identification of the receptor for the polypeptide of the present invention. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to SCGF polypeptides, and a cDNA library created from this RNA is divided into pools and used to transfect COS cells or other cells that are not responsive to SCGF. Transfected cells which are grown on glass slides are exposed to labeled SCGF. SCGF can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled SCGF can be photoaffinity linked with cell membrane or extract preparations that express the receptor molecule. Cross-linked material is resolved by PAGE and exposed to X-ray film. The labeled complex containing the SCGF-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which bind to and activate the SCGF receptors. An example of such a method takes advantage of the ability of SCGF to stimulate the proliferation of endothelial cells in the presence of the comitogen Con A. Human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^3$[H]-thymidine and harvested onto glass fiber filters (PhD; Cambridge Technology, Watertown, Mass.). Mean $^3$[H]-thymidine incorporation (cpm) of triplicate cultures is determined using a liquid scintillation counter (Beckman Instruments, Irvine, Calif.). Significants $^3$[H]-thymidine incorporation indicates stimulation of endothelial cell proliferation.

To assay for antagonists, the assay described above is performed, however, in this assay SCGF is added along with the compound to be screened and the ability of the compound to inhibit $^3$[H]-thymidine incorporation in the presence of SCGF, indicates that the compound is an antagonist to SCGF. Alternatively, SCGF antagonists may be detected by combining SCGF and a potential antagonist with membrane-bound SCGF receptors or recombinant receptors under appropriate conditions for a competitive inhibition assay. SCGF can be labeled, such as by radioactivity, such that the number of SCGF molecules bound to the receptor can determine the effectiveness of the potential antagonist.

Examples of potential SCGF antagonists include an antibody, or in some cases, an oligonucleotide, which binds to the polypeptide. Alternatively, a potential antagonist may be a closely related protein, for example, a mutated form of SCGF, which recognizes the SCGF receptor but imparts no effect, thereby competitively inhibiting the action of SCGF.

Another potential SCGF antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al. Science, 241:456 (1988); and Dervan et al., Science, 251:1360 (1991)), thereby preventing transcription and the production of SCGF. The antisense RNA oligonucleotide hybridizes to the mRNA in vivo and blocks translation of the mRNA molecule into the SCGF (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of SCGF.

Potential SCGF antagonists include small molecules which bind to the active site, the receptor binding site, or other growth factor binding site of the polypeptide thereby blocking the normal biological activity of SCGF. Examples of small molecules include but are not limited to small peptides or peptide-like molecules.

The antagonists may be employed to inhibit tumor neovascularization and the neointimal proliferation of smooth muscle cells prevalent in atherosclerosis and restenosis subsequent to balloon angioplasty.

The antagonists may also be employed to inhibit the over production of scar tissue seen in a keloid which forms after surgery, fibrosis after myocardial infarction, or fibrotic lesions associated with pulmonary fibrosis. The antagonists may be employed in a composition with a pharmaceutically acceptable carrier, e.g., as hereinafter described.

The SCGF polypeptides and antagonist or agonists of the present invention may be employed in combination with a suitable pharmaceutical carrier. Such compositions comprise a therapeutically effective amount of the polypeptide, agonist and antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, The pharmaceutical intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

SCGF in combination with other growth factors including but not limited to, PDGF, IGF, FGF, EGF or TGF-β may accelerate physiological responses as seen in wound healing.

The SCGF polypeptide and agonists and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmed vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRS hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAml2, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblaStB, keratinocytes, endothelial cells, and bronchial epithelial cells.

This invention is also related to the use of the gene of the present invention as a diagnostic. Detection of a mutation in the nucleic acid sequence encoding a polypeptide of the present invention will allow a diagnosis of a disease or a susceptibility to a disease, such as a tumor, since mutations in SCGF may cause tumors.

Individuals carrying mutations in the human SCGF gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding SCGF can be used to identify and analyze SCGF mutations. For example, deletions and insertions can be detected by a change in size of the amplified product in comparison to the normal genotype. Point mutations can be identified by hybridizing amplified DNA to radiolabeled SCGF RNA or alternatively, radiolabeled SCGF antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

SCGF protein expression may be linked to vascular disease or neovascularization associated with tumor formation. SCGF may have oncogenic effects on kidney, lung, heart or brain. Tissues in embryos are rapidly growing and an SCGF specific antibody could detect tumors which grow quickly. SCGF has a signal peptide and the mRNA is highly expressed in endothelial cells and to a lesser extent in smooth muscle cells. Accordingly, an anti-SCGF antibody could be used to diagnose vascular disease or neovascularization associated with tumor formation since an altered level of this polypeptide may be indicative of such disorders. Further, the SCGF protein is thought to be involved in tissue remodeling processes such as restenosis, hypertension, congestive heart failure and atherosclerosis.

A competition assay may be employed wherein antibodies specific to SCGF are attached to a solid support and labeled SCGF and a sample derived from the host are passed over the solid support and the amount of label detected attached to the solid support can be correlated to a quantity of SCGF in the sample.

A "sandwich" assay is similar to an ELISA assay. In a "sandwich" assay the SCGF polypeptide is passed over a solid support and binds to antibody attached to a solid support. A second antibody is then bound to the SCGF polypeptide. A third antibody which is labeled and specific to the second antibody is then passed over the solid support and binds to the second antibody and an amount can then be quantified.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3I untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptider, into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to imunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmed or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

17

Unless otherwise stated, transformation was performed as described in the method of Graham, F. and Van der Eb, A., Virology, 52:456–457 (1973).

EXAMPLE 1
Bacterial Expression and Purification of SCGF

The DNA sequence encoding SCGF, ATCC was initially amplified using PCR oligonucleotide primers corresponding to the 5' sequences of the processed SCGF protein (minus the signal peptide sequence) and the vector sequences 3' to the SCGF gene. Additional nucleotides corresponding to SCGF were added to the 5' and 3' sequences respectively. The 5' oligonucleotide primer has the sequence 5' CACTG-CAAGCTTATTTAAAAATGATGCCACAGAA 3' (SEQ ID NO:3) contains a Hind III restriction enzyme site (in bold) followed by 21 nucleotides of SCGF coding sequence starting from the presumed terminal amino acid of the processed protein codon (underlined). The 3' oligonucleotide primer 5' CATGCCTCTAGATATGGGAGTCT-GAGTTCTAAC 3' (SEQ ID NO:4) contains an Xba I restriction site (in bold) followed by the reverse complement of nucleotides corresponding to the carboxy terminal 5 amino acids and the translational stop codon (underlined). The restriction enzyme sites correspond to the restriction enzyme sites on the bacterial expression vector pQE9 (Qiagen, Inc. Chatsworth, Calif..). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 and the SCGF PCR product were then digested with Hind III and Xba I and ligated together with T4 DNA ligase. The desired recombinants would contain the SCGF coding sequence inserted downstream from the histidine tag and the ribosome binding site. The ligation mixture was then used to transform E. coli strain M15 [pREP5] (Qiagen, Inc.) by the procedure described in Sambrook, J. et al., Molecular Cloning: A Laboratory Manual, Cold Spring Laboratory Press, (1989). M15[pREP5] contains multiple copies of the plasmid pREP5, which expresses the laci repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the laci repressor, clearing the P/O leading to increased gene expression. Cells were grown an extra 3 to 4 hours such that there is an exponential growth culture present. Cells were then harvested by centrifugation. The SCGF/6-Histidine-containing M15 [pREP4] cells were lysed in 6M GnHC1, 50 mM NaPO4 at pH 8.0. The lysate was loaded on a Nickel-Chelate column and the flow-through collected. The column was washed with 6M GnHC1, 50 mM Napo4at pH 8.0, 6.0 and 5.0. The SCGF fusion protein (>90% pure) was eluted at pH 2.0. For the purpose of renaturation, the pH 2.0 eluate was adjusted to 3 molar guanidine HCl, 100 mm sodium phosphate, 10 mmolar glutathione (reduced) and 2 mmolar glutathione (oxidized). After incubation in this solution for 12 hours the protein was dialyzed to 10 remolar sodium phosphate. To run the gel, the pellets were resuspended in SDS/NAOH and SDS-PAGE loading buffer, heat denatured, then electrophoresed on a 15% denaturing polyacrylamide gel. The proteins were visualized with Coomassie Brilliant Blue R-250 stain.

EXAMPLE 2
Cloning and expression of SCGF using the baculovirus expression system The DNA sequence encoding SCGF, ATCC was initially amplified using PCR oligonucleotide primers corresponding to the 5' and 3' sequences of the SCGF coding region. Additional nucleotides corresponding to SCGF were added to the 5' and 3' sequences respectively. The 5' oligonucleotide primer has the sequence 5' CATTCGCGGATCCBC-CATCATGCTTCCTCCTGCCATTCAT 3' (SEQ ID NO:5) contains a BamHI restriction enzyme site (in bold) followed by 21 nucleotides of SCGF coding sequence starting from the presumed initiating methionine of the unprocessed protein (underlined). The 3' oligonucleotide primer 5' CACT-GCCTCTAGATATGGGAGTCTGAGTTCTAAC 3' (SEQ ID NO:6) contains an Xba I restriction site followed by the reverse complement of nucleotides corresponding to the 16 3' untranslated nucleotides adjacent to the translational stop codon (underlined). The restriction enzyme sites correspond to the restriction enzyme sites on the baculovirus expression vector pA2 (Qiagen, Inc. Chatsworth, Calif.). The SCGF PCR product and pA2 were then digested with BamHI and Xba I and ligated together with T4 DNA ligase.

The sequence of the cloned fragment is confirmed by DNA sequencing.

5 ug of the plasmid pbac SCGF is cotransfected with 1.0 µg of a commercially available linearized baculovirus ("BaculoGold™ baculovirus DNA", Pharmingen, San Diego, Calif.) using the lipofection method (Feloner et al. Proc. Natl. Acad. Sci. U.S.A., 84:7413–7417 (1987)).

1 µg of BaculoGold™ virus DNA and 5 µg of the plasmid pBac SCGF are mixed in a sterile well of a microtiter plate containing 50 µl of serum free Grace's medium (Life Technologies Inc., Gaithersburg, Md.)—Afterwards 10 µl Lipofectin plus 90 µl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-SCGF at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 3
Expression of Recombinant SCGF in CHO cells

The vector pN346 is used for the expression of the SCGF protein. Plasmid pN346 is a derivative of the plasmid pSV2-dhfr (ATCC Accession No. 37146). Both plasmids contain the mouse dhfr gene under control of the SV40 early promoter. Chinese hamster ovary or other cells lacking dihydrofolate activity that are transfected with these plasmids can be selected by growing the cells in a selective medium (alpha minus MEM, Lift Technologies) supplemented with the chemotherapeutic agent methotrexate. The amplication of the DHFR genes in cells resistant to methotrexate (MTX) has been well documented (see, e.g., Alt, F.W., Kellems, R.M., Bertino, J.R., and Schimke, R.T., 1978, J. Biol. Chem. 253:1357–1370, Hamlin, J.L. and Ma, C. 1990, Biochem. et Biophys. Acta, 1097:107–143, Page, M.i. and Sydenham, M.A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the dhfr gene it is usually co-amplified and overexpressed. Subsequently, when the methotrexate is withdrawn, cell lines contain the amplified gene integrated into the chromosome(s).

Plasmid pN346 contains for the expression of the gene of interest a strong promoter of the long terminal repeat (LTR) of the Rouse Sarcoma Virus (Cullen, et al., Molecular and Cellular Biology, March 1985, 438–447) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pN346 is digested with the restriction enzyme BamHI and then dephosphorylated using calf intestinal phosphatase by procedures known in the art. The vector is then isolated from a 1% agarose gel.

The DNA sequence encoding the full length SCGF protein, ATCC #97173, is amplified using PCR oligonucleotide primers corresponding to the 5' and 3' sequences of the gene:

The 5' primer has the sequence 5' CATCGCGGATCCGC-CATC<u>ATG</u>CTTCCTCCTGCCATTCAT 3' (SEQ ID NO:7) and contains a BamHI restriction enzyme site (in bold) followed by 21 nucleotides resembling an efficient signal for the initiation of translation in eukaryotic cells (Kozak, M., J. Mol. Biol., 196:947–950, (1987)). The remaining nucleotides correspond to the amino terminal 7 amino acids including the translational initiation codon (underlined). The 3' primer has the sequence 5' CAC TGCGGATCCTATGG-GAGTCTGAGTTCTAAC 3' (SEQ ID NO:8) and contains a BamHI restriction site (in bold) and 21 nucleotides that are the reverse complement of 3' untranslated DNA starting 16 nucleotides downstream from the translational stop codon. The PCR product is digested with BamHI and purified on a 1% agarose gel using a commercially available kit ("Geneclean," BIO 101 Inc., La Jolla, Calif.). This fragment is then ligated to BamHI digested, phosphatased pN346 plasmid with T4 DNA ligase. XllBlue (Stratagene) E. coli are transformed and plated on LB, 50 µg/ml ampicillin plates. Colonies bearing the desired recombinant in the proper orientation are screened for by PCR with a 5' primer which corresponds to the Rous sarcoma virus promoter and a 3' primer which corresponds to the reverse complement of SCGF codons 73–79. The sequence of the cloned fragment is confirmed by DNA sequencing.

Transfection of CHO-dhfr-cells

Chinese hamster ovary cells lacking an active DHFR enzyme are used for transfection. 5 µg of the expression plasmid pN346SCGF are cotransfected with 0.5 µg of the plasmid pSVneo using the lipofectin method (Feloner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25, 50 nm, 100 nm, 200 nm, 400 nm). Clones growing at the highest concentrations of methotrexate are then transferred to new 6-well plates containing even higher concentrations of methotrexate (500 nM, 1 µM, 2 µM, 5 µM). The same procedure is repeated until clones grew at a concentration of 100 µM.

The expression of the desired gene product is analyzed by Western blot analysis and SDS-PAGE.

EXAMPLE 4
Tissue Localization of SCGF Gene Expression by Northern Blot Analysis A multiple tissue Northern blot (Clontech Laboratories, Inc., 4030 Fabian Way; Palo Alto, Calif. 94303) containing 2 ug of human adult brain, heart, placenta, lung, liver skeletal muscle, kidney, and pancreas poly A+ mRNA per lane is prehybridized in Church buffer (Church, G. M. Gilbert, W., Proc. Natl. Acad. Sci. U.S.A. 81, 1991–1995 (1984) at 60° C. for one hour. The DNA sequence coding for SCGF, ATCC#97173, is amplified from the full length cDNA cloned in pBluescript SK(−) using the M13 Forward (5' GTAA AACGACGGCCAGT 3') (SEQ ID NO:9) and Reverse (5' GGAAACAGCTATGACCATG 3') (SEQ ID NO:10) primers. Twenty-five nanograms of PCR product is random primer radiolabeled (Prime-It II, Stratagene Cloning Systems, 11011 North Torrey Pines Rd.; La Jolla, Calif. 92037) with $^{32}$P-dCTP. The heat denatured SCGF probe is added directly to the prehybridization buffer and incubated 16 hr at 60° C. Two ten minute washes are performed in 0.2× SSC, 0.1% SDS at 60° C. Autoradiography is performed at −80° C.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pKV-7 (Kirschmeier, P.T. et al, DNA, 7:219–25 (1988)) flanked by the long terminal repeats of the moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney reurine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HE101, which are then plated onto agar-containing kanamycin for the purpose of confirming that the vector had the gene of interest properly inserted.

The amphotropic pA317 or GP+am12 packaging cells are grown in tissue culture to confluent density in Dulbeccols Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quiqkly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

---

What is claimed is:

1. An isolated polynucleotide comprising a polynucleotide having at least a 95% identity to a member selected from the group consisting of:

(a) a polynucleotide encoding a polypeptide comprising amino acids 1 to 183 of SEQ ID NO:2; and (b) the complement of (a).

2. The isolated polynucleotide of claim 1 wherein said member is (a).

3. A method of making a recombinant vector comprising inserting the isolated polynucleotide of claim 2 into a vector, wherein said polynucleotide is DNA.

4. A recombinant vector comprising the polynucleotide of claim 2, wherein said polynucleotide is DNA.

5. A recombinant host cell comprising the polynucleotide of claim 2, wherein said polynucleotide is DNA.

6. A method for producing a polypeptide comprising expressing from the recombinant host cell of claim 5 the polypeptide encoded by said polynucleotide; said polypeptide having the ability to stimulate proliferation of endothelial cells in the presence of comitogen Con A.

7. The isolated polynucleotide of claim 1 wherein said member is (a) and the polypeptide comprises amino acids −23 to 183 of SEQ ID No:2.

8. The isolated polynucleotide of claim 1 comprising a polynucleotide encoding a polypeptide comprising amino acids 1 to 183 of SEQ ID NO:2.

9. A process for producing a polypeptide comprising:
expressing from a recombinant cell containing the polynucleotide of claim 8 the polypeptide encoded by said polynucleotide.

10. The isolated polynucleotide of claim 1, wherein the polynucleotide is DNA.

11. The isolated polynucleotide of claim 1 comprising a polynucleotide encoding a polypeptide comprising amino acids −23 to 183 of SEQ ID NO:2.

12. A process for producing a polypeptide comprising:
expressing from a recombinant cell containing the polynucleotide of claim 11 the polypeptide encoded by said polynucleotide.

13. The isolated polynucleotide of claim 1, wherein said polynucleotide is RNA.

14. The isolated polynucleotide of claim 1 comprising nucleotides 121 to 735 of SEQ ID NO:1.

15. The isolated polynucleotide of claim 1 comprising nucleotides 117 to 735 of SEQ ID NO:1.

16. The isolated polynucleotide of claim 1 comprising the nucleotide sequence according to SEQ ID NO:1.

17. An isolated polynucleotide comprising a polynucleotide having at least a 95% identity to a member selected from the group consisting of:

(a) a polynucleotide encoding the same mature SCGF polypeptide encoded by the human cDNA in ATCC Deposit No. 97173; and (b) the complement of (a).

18. The isolated polynucleotide of claim 17, wherein the member is (a).

19. The isolated polynucleotide of claim 17, wherein said polynucleotide comprises DNA identical to the coding portion of the human cDNA in ATCC Deposit No. 97173 which encodes a mature SCGF polypeptide.

20. A method for producing a SCGF polypeptide comprising expressing from a recombinant host cell containing the polynucleotide of claim 18 the polypeptide encoded by said polynucleotide; said polypeptide having the ability to stimulate proliferation of endothelial cells in the presence of comitogen Con A.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 900 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
CGCCAAACCT   CTATGGATAT   ATAAAGGGAA   GCTTGAGGAG   GAATTTCACA   GTTACAGTGC      60

AGAAGCAGAG   GCAAAAGAAT   TAACCAGCTC   TTCAGTCAAG   CAAATCCTCT   ACTCACCATG     120

CTTCCTCCTG   CCATTCATTT   CTATCTCCTT   CCCCTTGCAT   GCATCCTAAT   GAAAAGCTGT     180

TTGGCTTTTA   AAAATGATGC   CACAGAAATC   CTTTATTCAC   ATGTGGTTAA   ACCTGTTCCA     240

GCACACCCCA   GCAGCAACAG   CACGTTGAAT   CAAGCCAGAA   ATGGAGGCAG   GCATTTCAGT     300

AACACTGGAC   TGGATCGGAA   CACTCGGGTT   CAAGTGGGTT   GCCGGGAACT   GCGTTCCACC     360

AAATACATCT   CTGATGGCCA   GTGCACCAGC   ATCAGCCCTC   TGAAGGAGCT   GGTGTGTGCT     420

GGCGAGTGCT   TGCCCCTGCC   AGTGCTCCCT   AACTGGATTG   GAGGAGGCTA   TGGAACAAAG     480

TACTGGAGCA   GGAGGAGCTC   CCAGGAGTGG   CGGTGTGTCA   ATGACAAAAC   CCGTACCCAG     540
```

| AGAATCCAGC | TGCAGTGCCA | AGATGGCAGC | ACACGCACCT | ACAAAATCAC | AGTAGTCACT | 600 |
| --- | --- | --- | --- | --- | --- | --- |
| GCCTGCAAGT | GCAAGAGGTA | CACCCGGCAG | CACAACGAGT | CCAGTCACAA | CTTTGAGAGC | 660 |
| ATGTCACCTG | CCAAGCCAGT | CCAGCATCAC | AGAGAGCGGA | AAAGAGCCAG | CAAATCCAGC | 720 |
| AAGCACAGCA | TGAGTTAGAA | CTCAGACTCC | CATAACTAGA | CTTACTAGTA | ACCATCTGCT | 780 |
| TTACAGATTT | GATTGCTTGG | AAGACTCAAG | CCTGCCACTG | CTGTTTTCTC | ACTTGAAAGT | 840 |
| ATATGCTTTC | TGCTTTGATC | AAACCCAGCA | AGCTGTCTTA | AGTATCAGGA | CCTTCTTTGG | 900 |

( 2 ) INFORMATION FOR SEQ ID NO:2:

( i ) SEQUENCE CHARACTERISTICS:
        ( A ) LENGTH: 206 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Lys Pro Pro Ala Ile His Phe Tyr Leu Leu Pro Leu Ala Cys
        -20              -15                   -10

Ile Leu Met Lys Ser Cys Leu Ala Phe Lys Asn Asp Ala Thr Glu
         -5                   1                5

Ile Leu Tyr Ser His Val Val Lys Pro Val Pro Ala His Pro Ser
             10              15                  20

Ser Asn Ser Thr Leu Asn Gln Ala Arg Asn Gly Gly Arg His Phe
             25              30                  35

Ser Asn Thr Gly Leu Asp Arg Asn Thr Arg Val Gln Val Gly Cys
             40              45                  50

Arg Glu Leu Arg Ser Thr Lys Tyr Ile Ser Asp Gly Gln Cys Thr
             55              60                  65

Ser Ile Ser Pro Leu Lys Glu Leu Val Cys Ala Gly Glu Cys Leu
             70              75                  80

Pro Leu Pro Val Leu Pro Asn Trp Ile Gly Gly Gly Tyr Gly Thr
             85              90                  95

Lys Tyr Trp Ser Arg Arg Ser Ser Gln Glu Trp Arg Cys Val Asn
             100             105                 110

Asp Lys Thr Arg Thr Gln Arg Ile Gln Leu Gln Cys Gln Asp Gly
             115             120                 125

Ser Thr Arg Thr Tyr Lys Ile Thr Val Val Thr Ala Cys Lys Cys
             130             135                 140

Lys Arg Tyr Thr Arg Gln His Asn Glu Ser Ser His Asn Phe Glu
             145             150                 155

Ser Met Ser Pro Ala Lys Pro Val Gln His His Arg Glu Arg Lys
             160             165                 170

Arg Ala Ser Lys Ser Ser Lys His Ser Met Ser
             175             180
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:3:

CACTGCAAGC TTATTTAAAA ATGATGCCAC AGAA 34

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:4:

CATGCCTCTA GATATGGGAG TCTGAGTTCT AAC 33

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:5:

CATTCGCGGA TCCCCATCAT GCTTCCTCCT GCCATTCAT 39

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:6:

CACTGCCTCT AGATATGGGA GTCTGAGTTC TAAC 34

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:7:

CATCGCGGAT CCGCCATCAT GCTTCCTCCT GCCATTCAT 39

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( x i ) SEQUENCE DESCRIPTION: SEQ ID NO:8:

TGCGGATCCT ATGGGAGTCT GAGTTCTAAC 30

( 2 ) INFORMATION FOR SEQ ID NO:9:

( i ) SEQUENCE CHARACTERISTICS:
  ( A ) LENGTH: 17 base pairs
  ( B ) TYPE: nucleic acid
  ( C ) STRANDEDNESS: Not Relevant
  ( D ) TOPOLOGY: linear ( i i ) MOLECULE TYPE: DNA (genomic)

( x i ) SEQUENCE DESCRIPTION: SEQ ID NO:9:

GTAAAACGAC GGCCAGT                                                                            17

( 2 ) INFORMATION FOR SEQ ID NO:10:

( i ) SEQUENCE CHARACTERISTICS:
    ( A ) LENGTH: 19 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( x i ) SEQUENCE DESCRIPTION: SEQ ID NO:10:

GGAAACAGCT ATGACCATG                                                                          19

( 2 ) INFORMATION FOR SEQ ID NO:11:

( i ) SEQUENCE CHARACTERISTICS:
    ( A ) LENGTH: 379 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:11:

| Met | Ser | Ser | Ser | Thr | Phe | Arg | Thr | Leu | Ala | Val | Ala | Val | Thr | Leu |
|---|---|---|---|---|---|---|---|---|---|---|---|---|---|---|
| | | | | 5 | | | | | 10 | | | | | 15 |

| Leu | His | Leu | Thr | Arg | Leu | Ala | Leu | Ser | Thr | Cys | Pro | Ala | Ala | Cys |
|---|---|---|---|---|---|---|---|---|---|---|---|---|---|---|
| | | | | 20 | | | | | 25 | | | | | 30 |

| His | Cys | Pro | Leu | Glu | Ala | Pro | Lys | Cys | Ala | Pro | Gly | Val | Gly | Leu |
|---|---|---|---|---|---|---|---|---|---|---|---|---|---|---|
| | | | | 35 | | | | | 40 | | | | | 45 |

| Val | Arg | Asp | Gly | Cys | Gly | Cys | Cys | Lys | Val | Cys | Ala | Lys | Gln | Leu |
|---|---|---|---|---|---|---|---|---|---|---|---|---|---|---|
| | | | | 50 | | | | | 55 | | | | | 60 |

| Asn | Glu | Asp | Cys | Ser | Lys | Thr | Gln | Pro | Cys | Asp | His | Thr | Lys | Gly |
|---|---|---|---|---|---|---|---|---|---|---|---|---|---|---|
| | | | | 65 | | | | | 70 | | | | | 75 |

| Leu | Glu | Cys | Asn | Phe | Gly | Ala | Ser | Ser | Thr | Ala | Leu | Lys | Gly | Ile |
|---|---|---|---|---|---|---|---|---|---|---|---|---|---|---|
| | | | | 80 | | | | | 85 | | | | | 90 |

| Cys | Arg | Ala | Gln | Ser | Glu | Gly | Arg | Pro | Cys | Glu | Tyr | Asn | Ser | Arg |
|---|---|---|---|---|---|---|---|---|---|---|---|---|---|---|
| | | | | 95 | | | | | 100 | | | | | 105 |

| Ile | Tyr | Gln | Asn | Gly | Glu | Ser | Phe | Gln | Pro | Asn | Cys | Lys | His | Gln |
|---|---|---|---|---|---|---|---|---|---|---|---|---|---|---|
| | | | | 110 | | | | | 115 | | | | | 120 |

| Cys | Thr | Cys | Ile | Asp | Gly | Ala | Val | Gly | Cys | Ile | Pro | Leu | Cys | Pro |
|---|---|---|---|---|---|---|---|---|---|---|---|---|---|---|
| | | | | 125 | | | | | 130 | | | | | 135 |

| Gln | Glu | Leu | Ser | Leu | Pro | Asn | Leu | Gly | Cys | Pro | Asn | Pro | Arg | Leu |
|---|---|---|---|---|---|---|---|---|---|---|---|---|---|---|
| | | | | 140 | | | | | 145 | | | | | 150 |

| Val | Lys | Val | Ser | Gly | Gln | Cys | Cys | Glu | Glu | Trp | Val | Cys | Asp | Glu |
|---|---|---|---|---|---|---|---|---|---|---|---|---|---|---|
| | | | | 155 | | | | | 160 | | | | | 165 |

| Asp | Ser | Ile | Lys | Asp | Ser | Leu | Asp | Asp | Gln | Asp | Asp | Leu | Leu | Gly |
|---|---|---|---|---|---|---|---|---|---|---|---|---|---|---|
| | | | | 170 | | | | | 175 | | | | | 180 |

| Leu | Asp | Ala | Ser | Glu | Val | Glu | Leu | Thr | Arg | Asn | Asn | Glu | Leu | Ile |
|---|---|---|---|---|---|---|---|---|---|---|---|---|---|---|
| | | | | 185 | | | | | 190 | | | | | 195 |

| Ala | Ile | Gly | Lys | Gly | Ser | Ser | Leu | Lys | Arg | Leu | Pro | Val | Phe | Gly |
|---|---|---|---|---|---|---|---|---|---|---|---|---|---|---|

|  | | | | | | | | 200 | | | | 205 | | | | 210 |
|---|---|---|---|---|---|---|---|---|---|---|---|---|---|---|---|---|

Thr Glu Pro Arg Val Leu Phe Asn Pro Leu His Ala His Gly Gln
                       215                  220                   225

Lys Cys Ile Val Gln Thr Thr Ser Trp Ser Gln Cys Ser Lys Ser
                       230                  235                   240

Cys Gly Thr Gly Ile Ser Thr Arg Val Thr Asn Asp Asn Pro Glu
                       245                  250                   255

Cys Arg Leu Val Lys Glu Thr Arg Ile Cys Glu Val Arg Pro Cys
                       260                  265                   270

Gly Gln Pro Val Tyr Ser Ser Leu Lys Lys Gly Lys Lys Cys Ser
                       275                  280                   285

Lys Thr Lys Lys Ser Pro Glu Pro Val Arg Phe Thr Tyr Ala Gly
                       290                  295                   300

Cys Ser Ser Val Lys Lys Tyr Arg Pro Lys Tyr Cys Gly Ser Cys
                       305                  310                   315

Val Asp Gly Arg Cys Cys Thr Pro Leu Gln Thr Arg Thr Val Lys
                       320                  325                   330

Met Arg Phe Arg Cys Glu Asp Gly Glu Met Phe Ser Lys Asn Val
                       335                  340                   345

Met Met Ile Gln Ser Cys Lys Cys Asn Tyr Asn Cys Pro His Pro
                       350                  355                   360

Asn Glu Ala Ser Phe Arg Leu Tyr Ser Leu Phe Asn Asp Ile His
                       365                  370                   375

Lys Phe Arg Asp ( 2 ) INFORMATION FOR SEQ ID NO:12:

( i ) SEQUENCE CHARACTERISTICS:
        ( A ) LENGTH: 374 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:12:

Met Ser Ser Arg Ile Val Arg Glu Leu Ala Leu Val Val Thr Leu
                       5                    10                    15

Leu His Leu Thr Arg Val Gly Leu Ser Thr Cys Pro Ala Asp Cys
                       20                   25                    30

His Cys Pro Leu Glu Ala Pro Lys Cys Ala Pro Gly Val Gly Leu
                       35                   40                    45

Val Arg Asp Gly Cys Gly Cys Cys Lys Val Cys Ala Lys Gln Leu
                       50                   55                    60

Asn Glu Asp Cys Arg Lys Thr Gln Pro Cys Asp His Thr Lys Gly
                       65                   70                    75

Leu Glu Cys Asn Phe Gly Ala Ser Ser Thr Ala Leu Lys Gly Ile
                       80                   85                    90

Cys Arg Ala Gln Ser Glu Gly Arg Pro Cys Glu Tyr Asn Ser Arg
                       95                   100                   105

Ile Tyr Gln Asn Gly Glu Ser Phe Gln Pro Asn Cys Lys His Gln
                       110                  115                   120

Cys Thr Cys Ile Gly Trp Arg Arg Gly Ala Cys Ile Pro Leu Cys
                       125                  130                   135

Pro Gln Glu Leu Ser Leu Pro Asn Leu Gly Cys Pro Asn Pro Arg
                       140                  145                   150

Leu Val Lys Val Thr Gly Gln Cys Cys Glu Glu Trp Val Cys Asp
                    155                 160                 165

Glu Asp Ser Ile Lys Asp Pro Met Glu Asp Gln Asp Gly Leu Leu
                    170                 175                 180

Gly Lys Gly Leu Gly Phe Asp Ala Ser Glu Val Glu Leu Thr Arg
                    185                 190                 195

Asn Asn Glu Leu Ile Ala Val Gly Lys Gly Ser Ser Leu Lys Arg
                    200                 205                 210

Leu Pro Val Phe Gly Met Glu Pro Arg Ile Leu Tyr Asn Pro Leu
                    215                 220                 225

Gln Gly Gln Lys Cys Ile Val Gln Thr Thr Ser Trp Ser Gln Cys
                    230                 235                 240

Ser Lys Thr Cys Gly Thr Gly Ile Ser Thr Arg Val Thr Asn Asp
                    245                 250                 255

Asn Pro Glu Cys Arg Leu Val Lys Glu Thr Arg Ile Cys Glu Val
                    260                 265                 270

Arg Pro Cys Gly Gln Pro Val Tyr Ser Ser Leu Lys Lys Gly Lys
                    275                 280                 285

Lys Cys Ser Lys Thr Lys Lys Ser Pro Glu Pro Val Arg Phe Thr
                    290                 295                 300

Tyr Ala Gly Cys Leu Ser Val Lys Lys Tyr Arg Pro Lys Tyr Cys
                    305                 310                 315

Gly Ser Cys Val Asp Gly Arg Cys Cys Thr Pro Gln Leu Thr Arg
                    320                 325                 330

Thr Val Lys Met Arg Phe Pro Cys Glu Asp Gly Glu Thr Phe Ser
                    335                 340                 345

Lys Asn Val Met Met Ile Gln Ser Ser Lys Cys Asn Tyr Asn Cys
                    350                 355                 360

Pro His Ala Asn Glu Ala Ala Phe Pro Phe Tyr Arg Leu Phe
                    365                 370

( 2 ) INFORMATION FOR SEQ ID NO:13:

( i ) SEQUENCE CHARACTERISTICS:
        ( A ) LENGTH: 375 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:13:

Met Gly Ser Ala Gly Ala Arg Pro Ala Leu Ala Ala Ala Leu Leu
                    5                   10                  15

Cys Leu Ala Arg Leu Ala Leu Gly Ser Pro Cys Pro Ala Val Cys
                    20                  25                  30

Gln Cys Pro Ala Ala Ala Pro Gln Cys Ala Pro Gly Val Gly Leu
                    35                  40                  45

Val Pro Asp Gly Cys Gly Cys Cys Lys Val Cys Ala Lys Gln Leu
                    50                  55                  60

Asn Glu Asp Cys Ser Arg Thr Gln Pro Cys Asp His Thr Lys Gly
                    65                  70                  75

Leu Glu Cys Asn Phe Gly Ala Ser Pro Ala Ala Thr Asn Gly Ile
                    80                  85                  90

Cys Arg Ala Gln Ser Glu Gly Arg Pro Cys Glu Tyr Asn Ser Lys
                    95                  100                 105

Ile Tyr Gln Asn Gly Glu Ser Phe Gln Pro Asn Cys Lys His Gln

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 110 |     |     |     | 115 |     |     |     | 120 |     |     |
| Cys | Thr | Cys | Ile | Asp | Gly | Ala | Val | Gly | Ile | Pro | Leu | Cys | Pro |     |
|     |     |     |     | 125 |     |     |     | 130 |     |     |     | 135 |     |     |
| Gln | Glu | Leu | Ser | Leu | Pro | Asn | Leu | Gly | Cys | Pro | Ser | Pro | Arg | Leu |
|     |     |     |     | 140 |     |     |     | 145 |     |     |     | 150 |     |     |
| Val | Lys | Val | Pro | Gly | Gln | Cys | Cys | Glu | Glu | Trp | Val | Cys | Asp | Glu |
|     |     |     |     | 155 |     |     |     | 160 |     |     |     | 165 |     |     |
| Ser | Lys | Asp | Ala | Leu | Glu | Glu | Leu | Glu | Gly | Phe | Phe | Ser | Lys | Glu |
|     |     |     |     | 170 |     |     |     | 175 |     |     |     | 180 |     |     |
| Phe | Gly | Leu | Asp | Ala | Ser | Glu | Gly | Glu | Leu | Thr | Arg | Asn | Asn | Glu |
|     |     |     |     | 185 |     |     |     | 190 |     |     |     | 195 |     |     |
| Leu | Ile | Ala | Ile | Val | Lys | Gly | Gly | Leu | Lys | Met | Leu | Pro | Val | Phe |
|     |     |     |     | 200 |     |     |     | 205 |     |     |     | 210 |     |     |
| Gly | Ser | Glu | Pro | Gln | Ser | Arg | Ala | Phe | Glu | Asn | Pro | Lys | Cys | Ile |
|     |     |     |     | 215 |     |     |     | 220 |     |     |     | 225 |     |     |
| Val | Gln | Thr | Thr | Ser | Trp | Ser | Gln | Cys | Ser | Lys | Thr | Cys | Gly | Thr |
|     |     |     |     | 230 |     |     |     | 235 |     |     |     | 240 |     |     |
| Gly | Ile | Ser | Thr | Arg | Val | Thr | Asn | Asp | Asn | Pro | Asp | Cys | Lys | Leu |
|     |     |     |     | 245 |     |     |     | 250 |     |     |     | 255 |     |     |
| Ile | Lys | Glu | Thr | Arg | Ile | Cys | Glu | Val | Arg | Pro | Cys | Gly | Gln | Pro |
|     |     |     |     | 260 |     |     |     | 265 |     |     |     | 270 |     |     |
| Ser | Tyr | Ala | Ser | Leu | Lys | Lys | Gly | Lys | Lys | Cys | Thr | Lys | Thr | Lys |
|     |     |     |     | 275 |     |     |     | 280 |     |     |     | 285 |     |     |
| Lys | Ser | Pro | Ser | Pro | Val | Arg | Phe | Thr | Tyr | Ala | Gly | Cys | Ser | Ser |
|     |     |     |     | 290 |     |     |     | 295 |     |     |     | 300 |     |     |
| Val | Lys | Lys | Tyr | Arg | Pro | Lys | Tyr | Cys | Gly | Ser | Cys | Val | Asp | Gly |
|     |     |     |     | 305 |     |     |     | 310 |     |     |     | 315 |     |     |
| Arg | Cys | Cys | Thr | Pro | Gln | Gln | Thr | Arg | Thr | Val | Lys | Ile | Arg | Phe |
|     |     |     |     | 320 |     |     |     | 325 |     |     |     | 330 |     |     |
| Arg | Cys | Asp | Asp | Gly | Glu | Thr | Phe | Thr | Lys | Ser | Val | Met | Met | Ile |
|     |     |     |     | 335 |     |     |     | 340 |     |     |     | 345 |     |     |
| Gln | Ser | Cys | Arg | Cys | Asn | Tyr | Asn | Cys | Pro | His | Ala | Asn | Glu | Ala |
|     |     |     |     | 350 |     |     |     | 355 |     |     |     | 360 |     |     |
| Tyr | Pro | Phe | Tyr | Arg | Leu | Val | Asn | Asp | Ile | His | Lys | Phe | Arg | Asp |
|     |     |     |     | 365 |     |     |     | 370 |     |     |     | 375 |     |     |

( 2 ) INFORMATION FOR SEQ ID NO:14:

( i ) SEQUENCE CHARACTERISTICS:
        ( A ) LENGTH: 348 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:14:

|     |     |     |     |     |     |     |     |     |     |     |     |     |     |     |
|-----|-----|-----|-----|-----|-----|-----|-----|-----|-----|-----|-----|-----|-----|-----|
| Met | Thr | Ala | Ala | Ser | Met | Gly | Pro | Val | Arg | Val | Ala | Phe | Val | Val |
|     |     |     |     | 5   |     |     |     | 10  |     |     |     | 15  |     |     |
| Leu | Leu | Ala | Leu | Cys | Ser | Arg | Pro | Ala | Val | Gly | Gln | Asn | Cys | Ser |
|     |     |     |     | 20  |     |     |     | 25  |     |     |     | 30  |     |     |
| Gly | Pro | Cys | Arg | Cys | Pro | Asp | Glu | Pro | Ala | Pro | Arg | Cys | Pro | Ala |
|     |     |     |     | 35  |     |     |     | 40  |     |     |     | 45  |     |     |
| Gly | Val | Ser | Leu | Val | Asp | Gly | Cys | Gly | Cys | Cys | Arg | Val | Cys | Ala |
|     |     |     |     | 50  |     |     |     | 55  |     |     |     | 60  |     |     |
| Lys | Gln | Leu | Gly | Glu | Leu | Cys | Thr | Glu | Arg | Asp | Pro | Cys | Asp | Pro |
|     |     |     |     | 65  |     |     |     | 70  |     |     |     | 75  |     |     |

-continued

```
His Lys Gly Leu Phe Cys Asp Phe Gly Ser Pro Ala Asn Arg Lys
                80                      85                      90

Ile Gly Val Cys Thr Ala Lys Asp Gly Ala Pro Cys Ile Phe Gly
                95                     100                     105

Gly Thr Val Tyr Arg Ser Gly Glu Ser Phe Gln Ser Ser Cys Lys
               110                     115                     120

Tyr Gln Cys Thr Cys Leu Asp Gly Ala Val Gly Cys Met Pro Leu
               125                     130                     135

Cys Ser Met Asp Val Arg Leu Pro Ser Pro Asp Cys Pro Phe Pro
               140                     145                     150

Arg Arg Val Lys Leu Pro Gly Lys Cys Cys Glu Glu Trp Val Cys
               155                     160                     165

Asp Glu Pro Lys Asp Gln Thr Val Val Gly Pro Ala Leu Ala Ala
               170                     175                     180

Tyr Arg Leu Glu Asp Thr Phe Gly Pro Asp Pro Thr Met Ile Arg
               185                     190                     195

Ala Asn Cys Leu Val Gln Thr Thr Glu Trp Ser Ala Cys Ser Lys
               200                     205                     210

Thr Cys Gly Met Gly Ile Ser Thr Arg Val Thr Asn Asp Asn Ala
               215                     220                     225

Ser Cys Arg Leu Glu Lys Gln Ser Arg Leu Cys Met Val Arg Pro
               230                     235                     240

Cys Glu Ala Asp Leu Glu Glu Asn Ile Lys Lys Gly Lys Lys Cys
               245                     250                     255

Ile Arg Thr Pro Lys Ile Ser Lys Pro Ile Lys Phe Glu Leu Ser
               260                     265                     270

Gly Cys Thr Ser Met Lys Thr Tyr Arg Ala Lys Phe Cys Gly Val
               275                     280                     285

Cys Thr Asp Gly Arg Cys Cys Thr Pro His Arg Thr Thr Thr Leu
               290                     295                     300

Pro Val Glu Phe Lys Cys Pro Asp Gly Glu Val Met Lys Lys Asn
               305                     310                     315

Met Met Phe Ile Lys Thr Cys Ala Cys His Tyr Asn Cys Pro Gly
               320                     325                     330

Asp Asn Asp Ile Phe Glu Ser Leu Tyr Tyr Arg Lys Met Tyr Gly
               335                     340                     345

Asp Met Ala
```

( 2 ) INFORMATION FOR SEQ ID NO:15:

( i ) SEQUENCE CHARACTERISTICS:
        ( A ) LENGTH: 348 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:15:

```
Met Leu Ala Ser Val Ala Gly Pro Ile Ser Leu Ala Leu Val Leu
                 5                      10                      15

Leu Ala Leu Cys Thr Arg Pro Ala Thr Gly Gln Asp Cys Ser Ala
                20                      25                      30

Gln Cys Gln Cys Ala Ala Glu Ala Ala Pro His Cys Pro Ala Gly
                35                      40                      45

Val Ser Leu Val Leu Asp Gly Cys Gly Cys Cys Arg Val Cys Ala
```

-continued

| | | | | 50 | | | | 55 | | | | 60 |
|---|---|---|---|---|---|---|---|---|---|---|---|---|
| Lys | Gln | Leu | Gly | Glu | Leu | Cys | Thr | Glu | Arg | Asp | Pro | Cys | Asp | Pro |

Lys Gln Leu Gly Glu Leu Cys Thr Glu Arg Asp Pro Cys Asp Pro
                    65                  70                  75
His Lys Gly Leu Phe Cys Asp Phe Gly Ser Pro Ala Asn Arg Lys
                    80                  85                  90
Ile Gly Val Cys Thr Ala Lys Asp Gly Ala Pro Cys Val Phe Gly
                    95                 100                 105
Gly Ser Val Tyr Arg Ser Gly Glu Ser Phe Gln Ser Ser Cys Lys
                   110                 115                 120
Tyr Gln Cys Thr Cys Leu Asp Gly Ala Val Gly Cys Val Pro Leu
                   125                 130                 135
Cys Ser Met Asp Val Arg Leu Pro Ser Pro Asp Cys Pro Phe Pro
                   140                 145                 150
Arg Arg Val Lys Leu Pro Gly Lys Cys Cys Lys Glu Trp Val Cys
                   155                 160                 165
Asp Glu Pro Lys Asp Arg Thr Ala Val Gly Pro Ala Leu Ala Ala
                   170                 175                 180
Tyr Arg Leu Glu Asp Thr Phe Gly Pro Asp Pro Thr Met Met Arg
                   185                 190                 195
Ala Asn Cys Leu Val Gln Thr Thr Glu Trp Ser Ala Cys Ser Lys
                   200                 205                 210
Thr Cys Gly Met Gly Ile Ser Thr Arg Val Thr Asn Asp Asn Thr
                   215                 220                 225
Phe Cys Arg Leu Glu Lys Gln Ser Arg Leu Cys Met Val Arg Pro
                   230                 235                 240
Cys Glu Ala Asp Leu Glu Glu Asn Ile Lys Lys Gly Lys Lys Cys
                   245                 250                 255
Ile Arg Thr Pro Lys Ile Ala Lys Pro Val Lys Phe Glu Leu Ser
                   260                 265                 270
Gly Cys Thr Ser Val Lys Thr Tyr Arg Ala Lys Phe Cys Gly Val
                   275                 280                 285
Cys Thr Asp Gly Arg Cys Cys Thr Pro His Arg Thr Thr Thr Leu
                   290                 295                 300
Pro Val Glu Phe Lys Cys Pro Asp Gly Glu Ile Met Lys Lys Asn
                   305                 310                 315
Met Met Phe Ile Lys Thr Cys Ala Cys His Tyr Asn Cys Pro Gly
                   320                 325                 330
Asp Asn Asp Ile Phe Glu Ser Leu Tyr Tyr Arg Lys Met Tyr Gly
                   335                 340                 345
Asp Met Ala ( 2 ) INFORMATION FOR SEQ ID NO:16:

( i ) SEQUENCE CHARACTERISTICS:
        ( A ) LENGTH: 351 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:16:

Met Glu Thr Gly Gly Gly Gln Gly Leu Pro Val Leu Leu Leu Leu
                     5                  10                  15
Leu Leu Leu Leu Arg Pro Cys Glu Val Ser Gly Arg Glu Ala Ala
                    20                  25                  30

```
Cys Pro Arg Pro Cys  Gly Gly Arg Cys Pro  Ala Glu Pro Pro Arg
             35                   40                        45

Cys Ala Pro Gly Val  Pro Ala Val Leu Asp  Gly Cys Gly Cys Cys
             50                   55                        60

Leu Val Cys Ala Arg  Gln Arg Gly Glu Ser  Cys Ser Pro Leu Leu
             65                   70                        75

Pro Cys Asp Glu Ser  Gly Gly Leu Tyr Cys  Asp Arg Gly Pro Glu
             80                   85                        90

Asp Gly Gly Gly Ala  Gly Ile Cys Met Val  Leu Glu Gly Asp Asn
             95                  100                       105

Cys Val Phe Asp Gly  Met Ile Tyr Arg Asn  Gly Glu Thr Phe Gln
            110                  115                       120

Pro Ser Cys Lys Tyr  Gln Cys Thr Cys Arg  Asp Gly Gln Ile Gly
            125                  130                       135

Cys Leu Pro Arg Cys  Asn Leu Gly Leu Leu  Leu Pro Gly Pro Asp
            140                  145                       150

Cys Pro Phe Pro Arg  Lys Ile Glu Val Pro  Gly Glu Cys Cys Glu
            155                  160                       165

Lys Trp Val Cys Asp  Pro Arg Asp Glu Val  Leu Leu Gly Gly Phe
            170                  175                       180

Ala Met Ala Ala Tyr  Arg Gln Glu Ala Thr  Leu Gly Ile Asp Val
            185                  190                       195

Ser Asp Ser Ser Ala  Asn Cys Ile Glu Gln  Thr Thr Glu Trp Ser
            200                  205                       210

Ala Cys Ser Lys Ser  Cys Gly Met Gly Phe  Ser Thr Arg Val Thr
            215                  220                       225

Asn Arg Asn Gln Gln  Cys Glu Met Val Lys  Gln Thr Arg Leu Cys
            230                  235                       240

Met Met Arg Pro Cys  Glu Asn Glu Glu Pro  Ser Asp Lys Lys Gly
            245                  250                       255

Lys Lys Cys Ile Gln  Thr Lys Lys Ser Met  Lys Ala Val Arg Phe
            260                  265                       270

Glu Tyr Lys Asn Cys  Thr Ser Val Gln Thr  Tyr Lys Pro Arg Tyr
            275                  280                       285

Cys Gly Leu Cys Asn  Asp Gly Arg Cys Cys  Thr Pro His Asn Thr
            290                  295                       300

Lys Thr Ile Gln Val  Glu Phe Arg Cys Pro  Gln Gly Lys Phe Leu
            305                  310                       315

Lys Lys Pro Met Met  Leu Ile Asn Thr Cys  Val Cys His Gly Asn
            320                  325                       330

Cys Pro Gln Ser Asn  Asn Ala Phe Phe Gln  Pro Leu Asp Pro Met
            335                  340                       345

Ser Ser Glu Ala Lys  Ile
            350
```

( 2 ) INFORMATION FOR SEQ ID NO:17:

( i ) SEQUENCE CHARACTERISTICS:
        ( A ) LENGTH: 357 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:17:

```
Met Gln Ser Val Gln  Ser Thr Ser Phe Cys  Leu Arg Lys Gln Cys
```

|   |   |   |   | 5 |   |   |   |   | 10 |   |   |   |   | 15 |
|---|---|---|---|---|---|---|---|---|---|---|---|---|---|---|
| Leu | Cys | Leu | Thr | Phe | Leu | Leu | Leu | His | Leu | Leu | Gly | Gln | Val | Ala |
|   |   |   |   | 20 |   |   |   |   | 25 |   |   |   |   | 30 |
| Ala | Thr | Gln | Arg | Cys | Pro | Pro | Gln | Cys | Pro | Gly | Arg | Cys | Pro | Ala |
|   |   |   |   | 35 |   |   |   |   | 40 |   |   |   |   | 45 |
| Thr | Pro | Pro | Thr | Cys | Ala | Pro | Gly | Val | Arg | Ala | Val | Leu | Asp | Gly |
|   |   |   |   | 50 |   |   |   |   | 55 |   |   |   |   | 60 |
| Cys | Ser | Cys | Cys | Leu | Val | Cys | Ala | Arg | Gln | Arg | Gly | Glu | Ser | Cys |
|   |   |   |   | 65 |   |   |   |   | 70 |   |   |   |   | 75 |
| Ser | Asp | Leu | Glu | Pro | Cys | Asp | Glu | Ser | Ser | Gly | Leu | Tyr | Cys | Asp |
|   |   |   |   | 80 |   |   |   |   | 85 |   |   |   |   | 90 |
| Arg | Ser | Ala | Asp | Pro | Ser | Asn | Gln | Thr | Gly | Ile | Cys | Thr | Ala | Val |
|   |   |   |   | 95 |   |   |   |   | 100 |   |   |   |   | 105 |
| Glu | Gly | Asp | Asn | Cys | Val | Phe | Asp | Gly | Val | Ile | Tyr | Arg | Ser | Gly |
|   |   |   |   | 110 |   |   |   |   | 115 |   |   |   |   | 120 |
| Glu | Lys | Phe | Gln | Pro | Ser | Cys | Lys | Phe | Gln | Cys | Thr | Cys | Arg | Asp |
|   |   |   |   | 125 |   |   |   |   | 130 |   |   |   |   | 135 |
| Gly | Gln | Ile | Gly | Cys | Val | Pro | Arg | Cys | Gln | Leu | Asp | Val | Leu | Leu |
|   |   |   |   | 140 |   |   |   |   | 145 |   |   |   |   | 150 |
| Pro | Glu | Pro | Asn | Cys | Pro | Ala | Pro | Arg | Lys | Val | Glu | Val | Pro | Gly |
|   |   |   |   | 155 |   |   |   |   | 160 |   |   |   |   | 165 |
| Glu | Cys | Cys | Glu | Lys | Trp | Ile | Cys | Gly | Pro | Asp | Glu | Glu | Asp | Ser |
|   |   |   |   | 170 |   |   |   |   | 175 |   |   |   |   | 180 |
| Leu | Gly | Gly | Leu | Thr | Leu | Ala | Ala | Tyr | Arg | Pro | Glu | Ala | Thr | Leu |
|   |   |   |   | 185 |   |   |   |   | 190 |   |   |   |   | 195 |
| Gly | Val | Glu | Val | Ser | Asp | Ser | Ser | Val | Asn | Cys | Ile | Glu | Gln | Thr |
|   |   |   |   | 200 |   |   |   |   | 205 |   |   |   |   | 210 |
| Thr | Glu | Trp | Thr | Ala | Cys | Ser | Lys | Ser | Cys | Gly | Met | Gly | Phe | Ser |
|   |   |   |   | 215 |   |   |   |   | 220 |   |   |   |   | 225 |
| Thr | Arg | Val | Thr | Asn | Arg | Asn | Arg | Gln | Cys | Glu | Met | Leu | Lys | Gln |
|   |   |   |   | 230 |   |   |   |   | 235 |   |   |   |   | 240 |
| Thr | Arg | Leu | Cys | Met | Val | Arg | Pro | Cys | Glu | Gln | Glu | Pro | Glu | Gln |
|   |   |   |   | 245 |   |   |   |   | 250 |   |   |   |   | 255 |
| Pro | Thr | Asp | Lys | Lys | Gly | Lys | Lys | Cys | Leu | Arg | Thr | Lys | Lys | Ser |
|   |   |   |   | 260 |   |   |   |   | 265 |   |   |   |   | 270 |
| Leu | Lys | Ala | Ile | His | Leu | Gln | Phe | Lys | Asn | Cys | Thr | Ser | Leu | His |
|   |   |   |   | 275 |   |   |   |   | 280 |   |   |   |   | 285 |
| Thr | Tyr | Lys | Pro | Arg | Phe | Cys | Gly | Val | Cys | Ser | Asp | Gly | Arg | Cys |
|   |   |   |   | 290 |   |   |   |   | 295 |   |   |   |   | 300 |
| Cys | Thr | Pro | His | Asn | Thr | Lys | Thr | Ile | Gln | Ala | Glu | Phe | Gln | Cys |
|   |   |   |   | 305 |   |   |   |   | 310 |   |   |   |   | 315 |
| Ser | Pro | Gly | Gln | Ile | Val | Lys | Lys | Pro | Val | Met | Val | Ile | Gly | Thr |
|   |   |   |   | 320 |   |   |   |   | 325 |   |   |   |   | 330 |
| Cys | Thr | Cys | His | Thr | Asn | Cys | Pro | Lys | Asn | Asn | Glu | Ala | Phe | Leu |
|   |   |   |   | 335 |   |   |   |   | 340 |   |   |   |   | 345 |
| Gln | Glu | Leu | Glu | Leu | Lys | Thr | Thr | Arg | Gly | Lys | Met |   |   |   |
|   |   |   |   | 350 |   |   |   |   | 355 |   |   |   |   |   |

( 2 ) INFORMATION FOR SEQ ID NO:18:

( i ) SEQUENCE CHARACTERISTICS:
     ( A ) LENGTH: 184 AMINO ACIDS
     ( B ) TYPE: AMINO ACID
     ( C ) STRANDEDNESS:
     ( D ) TOPOLOGY: LINEAR (ii) MOLECULE TYPE: PROTEIN (xi) SEQUENCE DESCRIPTION: SEQ ID NO:18:

| Met | Lys | Ser | Val | Leu<br>5 | Leu | Leu | Thr | Thr | Leu<br>10 | Leu | Val | Pro | Ala | His<br>15 |
|---|---|---|---|---|---|---|---|---|---|---|---|---|---|---|
| Leu | Val | Ala | Ala | Trp<br>20 | Ser | Asn | Asn | Tyr | Ala<br>25 | Val | Asp | Cys | Pro | Gln<br>30 |
| His | Cys | Asp | Ser | Ser<br>35 | Glu | Cys | Lys | Ser | Ser<br>40 | Pro | Arg | Cys | Lys | Arg<br>45 |
| Thr | Val | Leu | Asp | Asp<br>50 | Cys | Gly | Cys | Cys | Arg<br>55 | Val | Cys | Ala | Ala | Gly<br>60 |
| Arg | Gly | Glu | Thr | Cys<br>65 | Tyr | Arg | Thr | Val | Ser<br>70 | Gly | Met | Asp | Gly | Met<br>75 |
| Lys | Cys | Gly | Pro | Gly<br>80 | Leu | Arg | Cys | Gln | Pro<br>85 | Ser | Asn | Gly | Glu | Asp<br>90 |
| Pro | Phe | Gly | Glu | Glu<br>95 | Phe | Gly | Ile | Cys | Lys<br>100 | Asp | Cys | Pro | Tyr | Gly<br>105 |
| Thr | Phe | Gly | Met | Asp<br>110 | Cys | Arg | Glu | Thr | Cys<br>115 | Asn | Cys | Gln | Ser | Gly<br>120 |
| Ile | Cys | Asp | Arg | Gly<br>125 | Thr | Gly | Lys | Cys | Leu<br>130 | Lys | Phe | Pro | Phe | Phe<br>135 |
| Gln | Tyr | Ser | Val | Thr<br>140 | Lys | Ser | Ser | Asn | Arg<br>145 | Phe | Val | Ser | Leu | Thr<br>150 |
| Glu | His | Asp | Met | Ala<br>155 | Ser | Gly | Asp | Gly | Asn<br>160 | Ile | Val | Arg | Glu | Glu<br>165 |
| Val | Val | Lys | Glu | Asn<br>170 | Ala | Ala | Gly | Ser | Pro<br>175 | Val | Met | Arg | Lys | Trp<br>180 |
| Leu | Asn | Pro | Arg | | | | | | | | | | | |

(2) INFORMATION FOR SEQ ID NO:19:

(i) SEQUENCE CHARACTERISTICS:
 (A) LENGTH: 291 AMINO ACIDS
 (B) TYPE: AMINO ACID
 (C) STRANDEDNESS:
 (D) TOPOLOGY: LINEAR (ii) MOLECULE TYPE: PROTEIN (xi) SEQUENCE DESCRIPTION: SEQ ID NO:19:

| Met | Gln | Arg | Ala | Arg<br>5 | Pro | Thr | Leu | Trp | Ala<br>10 | Ala | Ala | Leu | Thr | Leu<br>15 |
|---|---|---|---|---|---|---|---|---|---|---|---|---|---|---|
| Leu | Val | Leu | Leu | Arg<br>20 | Gly | Pro | Pro | Val | Ala<br>25 | Arg | Ala | Gly | Ala | Ser<br>30 |
| Ser | Gly | Gly | Leu | Gly<br>35 | Pro | Val | Val | Arg | Cys<br>40 | Glu | Pro | Cys | Asp | Ala<br>45 |
| Arg | Ala | Leu | Ala | Gln<br>50 | Cys | Ala | Pro | Pro | Pro<br>55 | Ala | Val | Cys | Ala | Glu<br>60 |
| Leu | Val | Arg | Glu | Pro<br>65 | Gly | Cys | Gly | Cys | Cys<br>70 | Leu | Thr | Cys | Ala | Leu<br>75 |
| Ser | Glu | Gly | Gln | Pro<br>80 | Cys | Gly | Ile | Tyr | Thr<br>85 | Glu | Arg | Cys | Gly | Ser<br>90 |
| Gly | Leu | Arg | Cys | Gln<br>95 | Pro | Ser | Pro | Asp | Glu<br>100 | Ala | Arg | Pro | Leu | Gln<br>105 |
| Ala | Leu | Leu | Asp | Gly<br>110 | Arg | Gly | Leu | Cys | Val<br>115 | Asn | Ala | Ser | Ala | Val<br>120 |
| Ser | Arg | Leu | Arg | Ala | Tyr | Leu | Leu | Pro | Ala | Pro | Pro | Ala | Pro | Gly |

|   |   |   |   | 125 |   |   |   |   | 130 |   |   |   |   | 135 |
|---|---|---|---|---|---|---|---|---|---|---|---|---|---|---|
| Asn | Ala | Ser | Glu | Ser | Glu | Glu | Asp | Arg | Ser | Ala | Gly | Ser | Val | Glu |
|   |   |   |   | 140 |   |   |   |   | 145 |   |   |   |   | 150 |
| Ser | Pro | Ser | Val | Ser | Ser | Thr | His | Arg | Val | Ser | Asp | Pro | Lys | Phe |
|   |   |   |   | 155 |   |   |   |   | 160 |   |   |   |   | 165 |
| His | Pro | Leu | His | Ser | Lys | Ile | Ile | Ile | Ile | Lys | Lys | Gly | His | Ala |
|   |   |   |   | 170 |   |   |   |   | 175 |   |   |   |   | 180 |
| Lys | Asp | Ser | Gln | Arg | Tyr | Lys | Val | Asp | Tyr | Glu | Ser | Gln | Ser | Thr |
|   |   |   |   | 185 |   |   |   |   | 190 |   |   |   |   | 195 |
| Asp | Thr | Gln | Asn | Phe | Ser | Ser | Glu | Ser | Lys | Arg | Glu | Thr | Glu | Tyr |
|   |   |   |   | 200 |   |   |   |   | 205 |   |   |   |   | 210 |
| Gly | Pro | Cys | Arg | Arg | Glu | Met | Glu | Asp | Thr | Leu | Asn | His | Leu | Lys |
|   |   |   |   | 215 |   |   |   |   | 220 |   |   |   |   | 225 |
| Phe | Leu | Asn | Val | Leu | Ser | Pro | Arg | Gly | Val | His | Ile | Pro | Asn | Cys |
|   |   |   |   | 230 |   |   |   |   | 235 |   |   |   |   | 240 |
| Asp | Lys | Lys | Gly | Phe | Tyr | Lys | Lys | Lys | Gln | Cys | Arg | Pro | Ser | Lys |
|   |   |   |   | 245 |   |   |   |   | 250 |   |   |   |   | 255 |
| Gly | Arg | Lys | Arg | Gly | Phe | Cys | Trp | Cys | Val | Asp | Lys | Tyr | Gly | Gln |
|   |   |   |   | 260 |   |   |   |   | 265 |   |   |   |   | 270 |
| Pro | Leu | Pro | Gly | Tyr | Thr | Thr | Lys | Gly | Lys | Glu | Asp | Val | His | Cys |
|   |   |   |   | 275 |   |   |   |   | 280 |   |   |   |   | 285 |
| Tyr | Ser | Met | Gln | Ser | Lys |   |   |   |   |   |   |   |   |   |
|   |   |   |   | 290 |   |   |   |   |   |   |   |   |   |   |

( 2 ) INFORMATION FOR SEQ ID NO:20:

( i ) SEQUENCE CHARACTERISTICS:
        ( A ) LENGTH: 206 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:20:

|   |   |   |   | 5 |   |   |   |   | 10 |   |   |   |   | 15 |
|---|---|---|---|---|---|---|---|---|---|---|---|---|---|---|
| Met | Leu | Pro | Pro | Ala | Ile | His | Phe | Tyr | Leu | Leu | Pro | Leu | Ala | Cys |
|   |   |   |   | 20 |   |   |   |   | 25 |   |   |   |   | 30 |
| Ile | Leu | Met | Lys | Ser | Cys | Leu | Ala | Phe | Lys | Asn | Asp | Ala | Thr | Glu |
|   |   |   |   | 35 |   |   |   |   | 40 |   |   |   |   | 45 |
| Ile | Leu | Tyr | Ser | His | Val | Val | Lys | Pro | Val | Pro | Ala | His | Pro | Ser |
|   |   |   |   | 50 |   |   |   |   | 55 |   |   |   |   | 60 |
| Ser | Asn | Ser | Thr | Leu | Asn | Gln | Ala | Arg | Asn | Gly | Gly | Arg | His | Phe |
|   |   |   |   | 65 |   |   |   |   | 70 |   |   |   |   | 75 |
| Ser | Asn | Thr | Gly | Leu | Asp | Arg | Asn | Thr | Arg | Val | Gln | Val | Gly | Cys |
|   |   |   |   | 80 |   |   |   |   | 85 |   |   |   |   | 90 |
| Arg | Glu | Leu | Arg | Ser | Thr | Lys | Tyr | Ile | Ser | Asp | Gly | Gln | Cys | Thr |
|   |   |   |   | 95 |   |   |   |   | 100 |   |   |   |   | 105 |
| Ser | Ile | Ser | Pro | Leu | Lys | Glu | Leu | Val | Cys | Ala | Gly | Glu | Cys | Leu |
|   |   |   |   | 110 |   |   |   |   | 115 |   |   |   |   | 120 |
| Pro | Leu | Pro | Val | Leu | Pro | Asn | Trp | Ile | Gly | Gly | Gly | Tyr | Gly | Thr |
|   |   |   |   | 125 |   |   |   |   | 130 |   |   |   |   | 135 |
| Lys | Tyr | Trp | Ser | Arg | Arg | Ser | Ser | Gln | Glu | Trp | Arg | Cys | Val | Asn |
|   |   |   |   | 140 |   |   |   |   | 145 |   |   |   |   | 150 |
| Asp | Lys | Thr | Arg | Thr | Gln | Arg | Ile | Gln | Leu | Gln | Cys | Gln | Asp | Gly |
|   |   |   |   | 155 |   |   |   |   | 160 |   |   |   |   | 165 |
| Ser | Thr | Arg | Thr | Tyr | Lys | Ile | Thr | Val | Val | Thr | Ala | Cys | Lys | Cys |

| | | | | | | | | | | | | |
|---|---|---|---|---|---|---|---|---|---|---|---|---|
| Lys | Arg | Tyr | Thr | Arg 170 | Gln | His | Asn | Ser 175 | Ser | His | Asn | Phe | Glu 180 |
| Ser | Met | Ser | Pro | Ala 185 | Lys | Pro | Val | Gln | His 190 | His | Arg | Glu | Arg | Lys 195 |
| Arg | Ala | Ser | Lys | Ser 200 | Ser | Lys | His | Ser | Met 205 | Ser |